United States Patent
Arsiwalla et al.

(10) Patent No.: US 11,968,995 B2
(45) Date of Patent: Apr. 30, 2024

(54) METHOD TO CONVERT INSECTS OR WORMS INTO NUTRIENT STREAMS AND COMPOSITIONS OBTAINED THEREBY

(71) Applicant: Bühler Insect Technology Solutions AG, Uzwil (CH)

(72) Inventors: Tarique Arsiwalla, Amsterdam (NL); Kees Wilhelmus Petrus Aarts, Amsterdam (NL)

(73) Assignee: Bühler AG, Uzwil (CH)

( * ) Notice: Subject to any disclaimer, the term of this patent is extended or adjusted under 35 U.S.C. 154(b) by 340 days.

(21) Appl. No.: 16/655,956

(22) Filed: Oct. 17, 2019

(65) Prior Publication Data

US 2020/0045987 A1 Feb. 13, 2020

Related U.S. Application Data

(62) Division of application No. 14/766,511, filed as application No. PCT/NL2014/050077 on Feb. 7, 2014, now Pat. No. 10,537,118.

(60) Provisional application No. 61/761,735, filed on Feb. 7, 2013.

(30) Foreign Application Priority Data

Feb. 7, 2013 (NL) .................................... 2010268

(51) Int. Cl.
| | | |
|---|---|---|
| *C07K 14/435* | (2006.01) | |
| *A23D 9/00* | (2006.01) | |
| *A23D 9/02* | (2006.01) | |
| *A23J 1/02* | (2006.01) | |
| *A23J 3/04* | (2006.01) | |
| *A23K 10/00* | (2016.01) | |
| *A23K 10/20* | (2016.01) | |
| *A23K 20/142* | (2016.01) | |
| *A23K 20/147* | (2016.01) | |
| *A23K 20/158* | (2016.01) | |
| *A23L 33/00* | (2016.01) | |
| *A23L 33/115* | (2016.01) | |
| *A23L 33/17* | (2016.01) | |
| *A23L 35/00* | (2016.01) | |
| *A61K 47/12* | (2006.01) | |
| *C11B 1/06* | (2006.01) | |
| *C11B 1/12* | (2006.01) | |

(52) U.S. Cl.
CPC ................. *A23D 9/02* (2013.01); *A23D 9/00* (2013.01); *A23J 1/02* (2013.01); *A23J 3/04* (2013.01); *A23K 10/00* (2016.05); *A23K 10/20* (2016.05); *A23K 20/142* (2016.05); *A23K 20/147* (2016.05); *A23K 20/158* (2016.05); *A23L 33/00* (2016.08); *A23L 33/115* (2016.08); *A23L 33/17* (2016.08); *A23L 35/00* (2016.08); *A61K 47/12* (2013.01); *C11B 1/06* (2013.01); *C11B 1/12* (2013.01); *A23V 2002/00* (2013.01)

(58) Field of Classification Search
CPC ........... A23K 10/20; A23L 33/17; A23D 9/00; C07K 14/43563
See application file for complete search history.

(56) References Cited

FOREIGN PATENT DOCUMENTS

| | | |
|---|---|---|
| CN | 1266855 A | 9/2000 |
| CN | 1297691 A | 6/2001 |
| CN | 101117612 A | 2/2008 |
| CN | 101406486 A | 4/2009 |
| CN | 101880590 A | 11/2010 |
| CN | 101880591 A | 11/2010 |
| CN | 101880593 A | 11/2010 |
| CN | 102827689 A | 12/2012 |
| CN | 102578361 B | 9/2013 |
| JP | 2009254348 A | 11/2009 |
| RU | 2345139 C2 | 1/2009 |
| WO | 2008091137 A1 | 7/2008 |
| WO | 2010104908 A1 | 9/2010 |
| WO | 2011006276 A1 | 1/2011 |

OTHER PUBLICATIONS

Paoletti et al. Nutrient content of earthworms. Proc. R. Soc. Lond. B (2003) 270, 249-257. (Year: 2003).*
Edwards, C. A. "Production of feed protein from animal waste by earthworms". Phil. Trans. R. Soc. Lond. B. 310 (1985) 299-307. (Year: 1985).*
Da Tech, "Acid Number to FFA Conversions/Biodiesel Chemistry", 2012, 4 pages, Retrieved from URL:http://www.make-biodiesel.org/Biodiesel-Chemistry/acid-number-to-ffa-conversions.html.
Goodman, "Temperature Scales", 2001, Retrieved from http://wwwl.appstate.edu/-goodmanj/440 I/notes/heat I/temperature.html.
Kroeckel et al., "When a turbot catches a fly: Evaluation of a pre-pupae meal of the Black Soldier Fly (*Hermetia illucens*) as fish meal substitute—Growth performance and chitin degradation in juvenile turbot(*Psetta maxima*)", Aquaculture, Sep. 4, 2012, pp. 345-352, vol. 364-365.
Lee, "6: Spray-Drying of Proteins", Rational Design of Stable Protein Formulations, 2002, pp. 135-158.

(Continued)

*Primary Examiner* — Rosanne Kosson
(74) *Attorney, Agent, or Firm* — The Webb Law Firm

(57) ABSTRACT

A fat-containing composition obtained by converting insects or worms into nutrient streams, such as a fat-containing, an aqueous protein-containing and a solid-containing fraction, including (a) squashing insects or worms thereby obtaining a pulp, the insects or worms reduced in size, (b) heating the pulp to 70-100° C., and (c) subjecting the heated pulp to a physical separation step with the proviso that the method does not contain enzymatic treatment of the pulp. The fat-containing fraction contains at least 80 wt. % insect or worm fat with at least 40 wt. % saturated fats. The aqueous protein fraction can be dried to obtain dried protein material, which contains at least 50 wt. % insect or worm protein-derived matter and at most 25 wt. % insect or worm fat based on dry weight. The protein has a pepsin digestibility of at least 50%. The resulting nutrient streams can be used in food, petfood, feed and pharmaceutical industry.

13 Claims, No Drawings

(56) References Cited

OTHER PUBLICATIONS

Li et al., "Bioconversion of dairy manure by black soldier fly (Diptera: Stratiomyidae) for biodiesel and sugar production", Waste Management, 2011, pp. 1316-1320, vol. 31, No. 6.
Newton et al., "Using the Black Soldier Fly, *Hermetia illucens*, as a Value-Added Tool for the Management of Swine Manure", 2005, p. 16, Para. 1-2, Fig. 2, Table 1, Retrieved from http://www.urbantilth.org/wp-content/uploads/2008/09/soldierfly-swine-manure-management.pdf.
Pretorius, "The Evaluation of Larvae of *Musca domestica* (Common House Fly) as Protein Source for Broiler Production", 2011, 107 pages, Retrieved from http://scholar.sun.ac.za/handle/10019.1/46243.
Report 368, "Insects as a sustainable feed ingredient in pig and poultry diets—a feasibility study", Livestock Research Wageningen UR, 2012, pp. 1-48, English-language Abstract.
St-Hilaire et al., "Fish Offal Recycling by the Black Soldier Fly Produces a Foodstuff High in Omega-3 Fatty Acids", Journal of the World Aquaculture Society, 2007, pp. 309-313, vol. 38, No. 2.

\* cited by examiner

METHOD TO CONVERT INSECTS OR WORMS INTO NUTRIENT STREAMS AND COMPOSITIONS OBTAINED THEREBY

CROSS-REFERENCE TO RELATED APPLICATIONS

This application is a divisional of U.S. patent application Ser. No. 14/766,511, filed Feb. 7, 2014, which is the United States national phase of International Application No. PCT/NL2014/050077, filed Feb. 7, 2014, which claims priority to Netherlands Patent Application No. 2010268 filed Feb. 7, 2013, and U.S. Provisional Patent Application No. 61/761,735, filed Feb. 7, 2013, the disclosures of which are hereby incorporated in their entireties by reference.

BACKGROUND OF THE INVENTION

Field of the Invention

The invention relates to the field of obtaining nutrients, feed and foodstuffs from insects or worms. In particular, the invention presents a method to convert insects or worms into nutrient streams, encompassing a fat-containing fraction, an aqueous protein fraction and/or a solid-containing fraction.

Description of the Related Art

In the past decades, there has been a growing interest to use insects and worms as a food source, especially in view of the growth of global population and malnutrition in the developing world. Since insects and worms are rich in proteins and sometimes fats, they represent a relatively high caloric value. Although in some populations it is common to consume insects and worms, e.g. in Africa, Asia, Australia, these are usually eaten as such, be it as a whole or in parts, or used in the preparation of dishes.

However, it is desirable to be able to process insects and worms on an industrial scale to produce nutrients, which subsequently may be used in the preparation of food or feed products.

From several publications, it is known to obtain some particular nutrients from insects, such as proteins or fats.

JP2009254348 A concerns obtaining proteins from bee larvae. Dried larvae are suspended in water, whereto a lypolytic enzyme is added to decompose the lipids. After that, a proteolytic enzyme is added to hydrolyse proteins and the resulting mixture is filtered and the protein is collected. RU 2345139 C2 describes the recovery of chitin from cultivated larvae. WO 2008/091137 concerns an ethanol extract from house fly larvae, which is obtained by drying the larvae, dissolving these in an organic solvent to remove fats and mixing the residue with ethanol to obtain the extract. WO 2011/006276 describes obtaining fatty acids from insect larvae, wherein the fatty acids are extracted using organic solvent.

It is however not known to fully utilise insects or worms and to convert these into several nutrient streams, such as proteins, fats and chitin, from which streams the nutrients can optimally and easily be recovered.

An object of the present invention is therefore to provide a method that converts insects or worms into nutrient streams, and preferably into two or three nutrient streams, being a fat-containing stream and a protein containing stream, which can further be separated into an aqueous protein stream and a solids-containing stream, such as chitin.

Another object of the invention is to provide a processing method for insects or worms that results in nutrients that are not contaminated with toxic substances and are safe to be used in preparation of various food or feed products and pharmaceuticals.

Yet another object of the invention is to provide a method that is simple, does not require costly equipment or reagents and can easily be scaled up in a large production facility.

SUMMARY OF THE INVENTION

Accordingly, the invention provides, in a first aspect, a method to convert insects or worms into nutrient streams, comprising the steps of:
(a) obtaining a pulp from insects or worms,
(b) heating the pulp to a temperature of 70-100° C., and
(c) subjecting the heated pulp to a physical separation step thereby obtaining a fat fraction, an aqueous protein fraction and a solid-containing fraction,
with the proviso that the method does not comprise enzymatic treatment of the pulp.

In another aspect, the present invention provides a fat-containing composition comprising at least 80 wt. % insect or worm fat based on dry weight, wherein at least 40 wt. % of total fat are saturated fats, the fat comprising at least 7 wt. % lauric acid C12:0, 5-30 wt. % palmitic acid C16:0, and 8-40 wt. % oleic acid C18:1 based on the total fat weight.

In yet another aspect, the invention provides a composition comprising at least 40 wt. % protein and at most 25 wt. % fat based on dry weight, wherein the protein and the fat are derived from insects or worms and the protein has a pepsin digestibility of at least 50%, as measured by the pepsin-HCl method.

In a further aspect, the invention provides the use of the compositions in food, petfood, feed or pharmaceutical products.

DETAILED DESCRIPTION OF THE INVENTION

The method according to the invention converts insects or worms into nutrient streams. The term "insects" refers to insects in any development stage, such as adult insects, insect larvae and insect pupae. Preferably, insect larvae or worms are used. While the method is suitable for all forms of insects, it is particularly suitable for insect larvae since these contain substantial amounts of chitine which is usually difficult to separate completely from the other ingredients such as fat fraction. A large variety of insects and worms can be used. Preferably, edible insects or edible worms are used. More preferably, the insects are flies, bugs, mosquitos, butterflies, moths, cicadas, termites, bees, ants, wasps, beetles, grasshoppers, or crickets. More preferably, the insects belong to the species: black soldier fly (*Hermetia illucens*), house fly (*Musca domestica*), morio worm (*Zophobas Morio*), mealworm (*Tenebrio Molitor*) or cricket (*Gryllida*). In a preferred embodiment, the insects belong to the species black soldier fly. The insects and worms are preferably cultivated, e.g. in an insect farm. The cultivation allows to control and reduces the risks associated with diseases of insects and with the toxicity of insect-derived foodstuffs, e.g. due to the presence insecticides, in contrast to insects harvested in the nature. The conversion of the insects or worms into nutrient streams can suitably be carried out in a reactor vessel, preferably suitable for continuous operation.

In step (a) a pulp from insects or worms is obtained. Preferably, the insects or worms are squashed to obtain a pulp. More preferably, the insects or worms are reduced in size, preferably by cutting and/or milling. This results in a homogeneous starting material of viscous consistency. The squashing and reducing in size can conveniently be done in a micro-cutter mill, although other suitable techniques can also be used. During this step, the particle size of the insect or worm remains in the pulp is preferably less than 1 mm (the largest size to be determined using a microscope), more preferably less than 0.5 mm. The particle size can be controlled by selection of a specific knife and plate combination and rotating speed; for example one can use a single or double knife in combination with a sieve mesh of at least 4 mm, preferably around 6 mm. The rotating speed could vary between 1000 and 3000 rpm. A skilled person can find suitable conditions in order to reach a desired particle size. A small particle size is advantageous as it facilitates fat extraction, however a too small particle size could create an emulsion making it more difficult to separate the fat in the next steps. Preferably, the particle size is at least 10 micron. The reduction in size can also be carried out as a separate step, preceding the heating step.

In the following step, step (b), the pulp is heated to a temperature in the range from 60 to 100° C., preferably in the range 80-95° C. The heating assures that the majority of fats is liquefied in order to prepare a suitable mixture for the following separation step. Preferably, the heating is affected under mixing conditions to promote separation of different phases. A skilled person will be able to determine suitable heating time. Preferably, the pulp is heated during 0.1-4 hours, for example 5-10 min. Typically, the pulp is heated gradually in 1-4 hours, preferably 1-3 hours towards 90° C.

In step (c), the heated pulp is subjected to a physical separation step to obtain nutrient streams. In the physical separation step different phases (oil, water, solid) are separated. Preferably, the nutrient streams are a fat-containing fraction, an aqueous protein fraction and a solid-containing fraction. The physical separation preferably encompasses decanting, centrifuging, or a combination of the two methods. It is preferred to avoid pressing of the pulp, which is sometimes used in the art to obtain oil. The inventors believe that pressing can increase the chances to damage the protein product and can also decrease the content of the available fat since fat could become locked in chitine. Therefore, the physical separation step is preferably performed at a normal (atmospheric) pressure.

In a preferred embodiment, first, a fat fraction is separated by decanting, and the remaining mixture is further separated into an aqueous protein fraction and a solid-containing fraction by decanting or centrifugation. However, the fat, protein and solid-containing fractions can also be obtained in a different order, or simultaneously, e.g. by using a 3-phase decanter. In another preferred embodiment, the physical separation into three phases is carried out by using a 3-phase decanter. This achieves a great advantage that the three streams are obtained with a minimum of steps (preferably only one step) and thus with minimal losses of the product. Reducing the number of separation steps has also advantages when used in a continuous process.

In a further preferred embodiment, a fat fraction is separated first, e.g. by decanting, and the remaining mixture is not further separated but subjected to drying. The remaining mixture therefore combines both the solid fraction and the aqueous protein fraction. In this embodiment, the non-fat phases are preferably further dried to produce dried material. The dried material is protein-rich and contains both the protein-rich material from the aqueous protein fraction and solids from the solid-containing fraction.

Drying can be effected by different methods, such as air drying, drum drying, disc drying, flash drying or spray drying. The aqueous protein fraction is preferably dried by spray drying. The solid-containing fraction is preferably dried by drum drying, although flash drying or other methods are also possible. If spray drying is used for drying the combined protein and solids material, it may be necessary to reduce the solid particles present in the mixture first to a required size. This can suitably be done by a micro-cutter mill using a relatively small sieve mesh, for example 1 mm. When using a micro-cutter, to obtain a suitable mixture of the aqueous protein fraction and solid fraction for further drying, both fractions could be dosed together into the micro-cutter; other mixing methods are also possible. The drying of the two (mixed) fractions together is preferably performed by spray drying.

In a preferred embodiment, one or more of the above described steps (a)-(c) are carried out in a continuous way. For example, the insects or worms are first milled, which is followed by a heat treatment in line.

The method according to the invention does not comprise enzymatic treatment of the pulp. In this way, the presented method does not require costly materials such as enzymes and is simple and economic in practice.

As a result of the phase separation in the last step, preferably a fat fraction, an aqueous protein fraction and a solid-containing fraction are obtained. In this way, the method results directly in several nutrient streams. Under nutrients streams in the present description streams are understood that contain nutrients, such as fats, protein and protein-derived material, carbohydrates, minerals and/or chitin. For the purposes of the present description, chitin is also considered a nutrient.

The fat-containing fraction predominantly contains insect or worm fat. Under "predominantly containing", e.g. fat, it is understood that based on the dry weight, the stream contains more fat (on a weight basis) than any other component, or in other words, that fat constitutes the major part of all ingredients based on dry weight. Generally, "predominantly containing" means a content of at least 40 wt. % dry matter, more preferably at least 50 wt. % dry matter. The aqueous protein fraction predominantly contains protein.

The fat-containing fraction obtainable by the method according to the invention, preferably comprises at least 80 wt. %, more preferably at least 85 wt. %, yet more preferably 90-100 wt. % of insect or worm fat based on the dry weight of the fat fraction. The insect or worm fat in the fat fraction comprises at least 40 wt. % and preferably 50-80 wt. % saturated fats, based on the total weight of the fat. The amount of unsaturated fats is 60 wt. % or less, preferably less than 50 wt. % and more preferably 20-40 wt. %, based on the total weight of the fat. The amount of mono unsaturated fatty acids (cis) is preferably from 10 to 45 wt. %, more preferably from 15 to 30 wt. %, while the amount poly unsaturated fatty acids is preferably from 1 to 20 wt. %, more preferably from 5 to 15 wt. %.

In a preferred embodiment, the insect or worm fat contains at least 7 wt. %, preferably 8-60 wt. %, more preferably 15-55 wt. %, yet more preferably 30-50 wt. % of lauric acid C12:0. The insect or worm fat preferably contains 5-30 wt. %, more preferably 10-20 wt. % of palmitic acid C16:0. Further, the insect or worm fat may further comprise omega-9 fatty acids, preferably in an amount 5-45 wt. %, more preferably 10-30 wt. %. Under omega-9 fatty acids, the sum of the following acids is understood: oleic acid C18:1, eicosenoic acid C20:1, mead acid C20:3, erucic acid C22:1, nervonic acid C24:1. In particular, the insect or worm fat preferably contains 8-40 wt. % oleic acid C18:1, more preferably, 10-35 wt. %, yet more preferably 13-20 wt. %. Omega-6 fatty acids are preferably present in an amount 2-20 wt. %, more preferably 5-10 wt. %. Under omega-6 fatty acids, the sum of the following acids is understood: linoleic acid C18:2, gamma-linolenic acid C18:3, eicosadienoic acid C20:2, dihomo-gamma-linolenic acid C20:3, arachidonic acid C20:4, docosadioenoic acid C22:2, adrenic acid C22:4, docosapentaenoic acid C22:5, tetracosatetraenoic acid C24:4, tetracosapentaenoic acid C24:5. For example, linoleic acid C18:2 is preferably present in an amount 5-15 wt. %. The amount of trans fatty acids is lower than 0.5 wt. %, preferably lower than 0.2 wt. %. Under trans fatty acids unsaturated fatty acids are meant with at least one carbon-carbon double bond with a trans configuration, e.g. elaidic acid C18:1. The insect or worm fat is of exceptionally good quality and has a low free fatty acids (FFA) content, such as less than 1 wt. % of the total fat (calculated as oleic acid 282 g/mol), preferably less than 0.6 wt. %, more preferably less than 0.4 wt. %. The free fatty acids content can be measured by standard methods for example titrimetry. The peroxide value is preferably less than 3 meq/kg total fat, preferably less than 2 meq/kg total fat. For the measurement of peroxide value standard methods are used, such as the AOCS method. The amounts of fatty acids are based on the weight of the insect or worm fat, which is the fat component of the fat-containing fraction. The fatty acid composition is determined by a standard method NEN-EN-ISO 5508+5509, BF3.

Another fraction obtained in the separation step is an aqueous protein fraction. Apart from protein, this fraction may comprise other proteinaceous matter such as peptides, amino acids and/or other protein-derived compounds. The aqueous protein fraction can further be dried to obtain dried protein material. This dried material can itself be used as a food or feed ingredient, or it can further be processed, e.g. to isolate amino acids. The aqueous fraction is preferably dried by spray drying.

The dried protein material contains at least 40 wt. %, preferably at least 45 wt. %, more preferably at least 50 wt. % such as 50-85 wt. % of insect or worm protein. Under "insect or worm protein" and "insect or worm fat" respectively protein and fat derived from insects or worms are meant. The amount of fat present in the protein material may vary and depends in particular on the degree of phase separation of the heated pulp by decanting or other physical methods. The degree of fat separation from the heated pulp depends, amongst others, on the cutting-size of the insects, the heating temperature and time of the pulp and the (three-phase) decanter settings. An experienced operator can find the right combinations of settings to maximize the fat separation without harming the proteins and other nutrients. It is preferred to limit the fat content of the protein material to at most 25 wt. %, preferably at most 20, yet more preferably at most 10 wt. % of insect or worm fat, based on dry weight. In particular, higher temperatures and longer times during step (b) may be applied to improve the separation of fats from the aqueous phase and, consequently, to increase the protein content in the final dried protein material. The dried protein material is preferably in the form of powder and may further comprise residual moisture, minerals and/or carbohydrates. Preferably, the powder contains less than 8 wt. % moisture, more preferably less than 5 wt. %, most preferably less than 2 wt. %. Preferably, the protein does not comprise hydrolysed protein matter. The protein is preferably in a substantially intact form, that is, at least 90% and more preferably at least 95% of the protein is intact, that is, not in the form of peptides or amino acids, which is determined by mass spectrometry.

The insect or worm protein in the composition above has preferably a pepsin digestibility of at least 50% as determined by a standard "pepsin-HCl" laboratory test such as following the guideline in the Third Commission Directive 72/199/EEC of 27 Apr. 1972.

In a preferred embodiment, the dried protein material contains at least 50 wt. % insect or worm protein, which protein has a protein digestibility of at least 70%, preferably 80-95%. Preferably, the protein material contains one or more amino acids selected from asparagine, lysine, isoleucine, methionine and tryptophan. In a preferred embodiment, the protein material is characterized by an amino acid profile, containing 2-7 wt. % lysine, preferably 2.5-4 wt. %, based on the total dry weight of the protein material.

In a particularly preferred embodiment, the protein material contains lysine and further isoleucine 0.4-0.8, threonine 0.5-0.8, tryptophan 0.1-0.3 and valine 0.5-1.2, as a weight ratio relative to the lysine content. Yet more preferably, the protein material has the following amino acid profile: alanine 1-1.2, asparagine 0.7-0.9, aspartic acid 1.4-1.7, cysteine 0.08-0.15, glutamic acid 1.5-3.5, glycine 0.8-1.1, histidine 0.4-0.7, isoleucine 0.4-0.8, leucine 0.6-1.3, methionine 0.05-0.4, phenylalanine 0.4-1.5, proline 1-1.2, serine 0.5-0.8, threonine 0.5-0.8, tryptophan 0.1-0.3, tyrosine 0.5-1.2, valine 0.5-1.2, the values being the weight ratio relative to lysine. This amino acid profile is particularly suitable for various food and feed applications as a protein or amino acids source. The amino acid profile is determined according to the method NEN-EN-ISO 13903.

In another preferred embodiment, the dried protein material further contains minerals such as calcium and/or phosphorus. Preferably, the calcium content of the protein material is at least 4,500, more preferably 60,000-30,000 mg/kg, based on dry weight of the protein material. The phosphorus content of the protein material is preferably at least 5000 mg/kg, based on dry weight. The calcium and phosphorus content is determined by the OCP-OES method.

The dried protein material may contain limited amounts of fats; preferably, the composition of this fat fraction is the same as described above for the fat-containing stream separated from the pulp. In particular, the fat fraction of the protein material preferably comprises at least 40 wt. % and preferably 50-80 wt. % saturated fats, based on the total weight of the fat. The amount of unsaturated fats is 60 wt. % or less, preferably less than 50 wt. % and more preferably 20-40 wt. %, based on the total weight of the fat. The amount of mono unsaturated fatty acids (cis) is preferably from 10 to 45 wt. %, more preferably from 15 to 30 wt. %, while the amount poly unsaturated fatty acids is preferably from 1 to 20 wt. %, more preferably from 5 to 15 wt. %. In a preferred embodiment, the insect or worm fat contains at least 7 wt. %, preferably 8-60 wt. %, more preferably 15-55 wt. %, yet more preferably 30-50 wt. % of lauric acid C12:0. The insect or worm fat preferably contains 5-30 wt. %, more preferably 10-20 wt. % of palmitic acid C16:0. Further, the insect or worm fat may further comprise omega-9 fatty acids, preferably in an amount 5-45 wt. %, more preferably 10-30 wt. %. Omega-6 fatty acids are preferably present in an amount 2-20 wt. %, more preferably 5-10 wt. %. The amount of trans fatty acids is lower than 0.5 wt. %, preferably lower than 0.2 wt. %. If desired, the fat fraction of the protein material can be isolated for further use.

The remaining solid-containing fraction obtained in the separation step (d), which step encompasses for example decanting or centrifugation, represents a wet pulp, or a suspension. This wet pulp can easily be distinguished and separated from the aqueous protein fraction. The wet pulp contains solids such as chitin and chitin-derivatives. Preferably, the solid-containing fraction contains 2-50 wt. %, preferably 5-40 wt. % chitin, based on dry weight. The wet pulp may further comprise protein and/or fat-containing matter. The protein matter preferably has the composition as described herein-above for the aqueous protein fraction, and the protein has a pepsin digestibility of the protein-derived matter in the range 50-95%, preferably 70-90% as can be determined by a standard "pepsin-HCl" laboratory test; and particularly by following the guideline in the Third Commission Directive 72/199/EEC of 27 Apr. 1972. The fat-containing matter preferably has the composition as described above for the fat-containing fraction obtained after physical separation of the pulp.

The solid-containing fraction can further be dried to obtain solid material. Preferably, air drying is used. The solid-containing fraction can also be further processed to isolate chitin. Chitin is a polysaccharide that can be used in various applications. In food industry, chitin can be used as an additive to thicken and stabilise foods and pharmaceuticals. It can also be used in animal feed as a nutrient source.

The advantage of the method of the invention is that by simple physical separation the bulk of insect of worm mass is separated into valuable nutrient streams, of which the fat fraction and the dried protein material may be of particular value. These streams are not contaminated with chemicals and are ready for use in further application without purification. The isolated nutrient streams can further be used in the preparation of food or feed, or of food or feed additives, or in pharmaceutical industry. Preferably, the compositions are used in an animal feed product. For example, the protein material and the fat fraction can, respectively, be used in animal feed as a crude protein and a crude fat source. The obtained streams can also be processed further, e.g. to isolate specific ingredients such as hydrolysed protein, amino acids, or specific fatty acids.

The invention is now illustrated in the following, non-limiting examples.

Example 1

1000 kg fresh larvae of black soldier fly are squashed and cut in a micro-cutter mill to obtain insect pulp with an average particle size less than 0.5 mm. The pulp is introduced in a reaction vessel and is heated to 90° C. during 1 hour and then brought into a decanter. From the decanter a fat fraction and a combined protein fraction are obtained. The combined protein fraction contains "larvae water" with mostly insect protein and a solid residue.

The composition of the fat fraction after disc centrifugation is given in Table 1. The fatty acids composition of the crude fat is given in Table 2, wherein the percentage is based on the weight of the crude fat. The fatty acids composition was determined by NEN-EN-ISO 5508+5509, BF3 method. The fatty acids are referred to as Cn:m, wherein n is the amount of carbon atoms, and n is the amount of unsaturated carbon-carbon bonds.

TABLE 1

| Component | Content (wt. %) |
|---|---|
| Moisture (after disc centrifuge) | n/a |
| Crude protein (Dumas, N × 6.25) | <0.5 |
| Crude fat (petroleum-ether extraction) | 99.1 |
| Crude fiber (long method) | <0.3 |
| Crude ashes (550° C.) | 0.2 |
| FFA (calculated as oleic acid 282 g/mol) | 0.5 |
| Peroxide value | 2.7 meq/kg fat |

TABLE 2

| Fatty acid | Content (wt. %) |
|---|---|
| C10:0 | 1.3 |
| C12:0 | 43.1 |
| C14:0 | 7.3 |
| C14:1 | 0.3 |
| C15:0 | 0.2 |
| C16:0 | 14.6 |
| C16:1 | 2.9 |
| C17:0 | <0.1 |
| C18:0 | 2.0 |
| C18:1 | 17.0 |
| C18:1 cis | 0.3 |
| C18:2 | 8.3 |
| C18:3n3 | 1.1 |
| C20:5 | 0.3 |
| trans fatty acids | <0.1 |
| saturated fatty acids | 68.7 |
| mono unsaturated fatty acids | 20.4 |
| poly unsaturated fatty acids | 9.8 |
| unsaturated fatty acids | 30.2 |
| omega-3 fatty acids | 1.5 |
| omega-6 fatty acids | 8.3 |
| omega-9 fatty acids | 17.0 |
| omega-3/omega-6 | 0.2 |

The combined protein fraction is further separated by decanting, into larvae water and a solid-containing fraction. The larvae water is spray-dried to obtain protein material with the composition as shown in Table 3. The fat composition of the crude fat fraction of the protein material is given in Table 4, wherein the percentages refer to percentages by weight based on the total weight of the crude fat fraction. The amino acid composition of the crude protein is given in Table 5, wherein the percentages refer to percentages by weight based on the total weight of the dried protein material. The amino acid profile is determined according to the method NEN-EN-ISO 13903.

TABLE 3

| Component | Content (wt. %) |
|---|---|
| Moisture (dry matter at 103° C.) | 7.7 |
| Crude protein (Dumas, N × 6.25) | 58 |
| Crude fat (after pre-extraction and hydrolysis) | 4.6 |
| Crude ashes (550° C.) | 13.2 |
| Crude fiber (long method) | <0.3 |
| FFA (calculated as oleic acid 282 g/mol) | 0.6 |
| Peroxide value | <0.1 meq/kg fat |
| Phosphorus, mg/kg | 6000 |
| Calcium, mg/kg | 7300 |

TABLE 4

| Fatty acid | Content (wt. %) |
|---|---|
| C8:0 | <0.1 |
| C10:0 | 1.3 |

TABLE 4-continued

| Fatty acid | Content (wt. %) |
| --- | --- |
| C12:0 | 40.9 |
| C14:0 | 7 |
| C14:1 | 0.2 |
| C15:0 | 0.2 |
| C16:0 | 15.0 |
| C16:1 | 2.8 |
| C17:0 | 0.1 |
| C18:0 | 2.4 |
| C18:1 | 17.7 |
| C18:1 cis | 0.3 |
| C18:2 | 8.3 |
| C18:3n3 | 1.0 |
| C20:0 | 0.2 |
| C20:3n3 | 0.1 |
| C20:5 | 0.3 |
| C22:0 | 0.2 |
| trans fatty acids | <0.1 |
| saturated fatty acids | 67.4 |
| mono unsaturated fatty acids | 21.0 |
| poly unsaturated fatty acids | 9.7 |
| unsaturated fatty acids | 30.8 |
| omega-3 fatty acids | 1.5 |
| omega-6 fatty acids | 8.3 |
| omega-9 fatty acids | 17.8 |
| omega-3/omega-6 | 0.2 |

TABLE 5

| Amino acid | Content (wt. %) | Content relative to lysine (wt/wt) |
| --- | --- | --- |
| Alanine | 3.29 | 1.12 |
| Asparagine | 2.32 | 0.79 |
| Aspartic acid | 4.32 | 1.47 |
| Cysteine | 0.30 | 0.10 |
| Glutamic acid | 10.05 | 3.43 |
| Glycine | 2.58 | 0.88 |
| Histidine | 1.97 | 0.67 |
| Isoleucine | 1.42 | 0.48 |
| Leucine | 1.84 | 0.63 |
| Lysine | 2.93 | 1.00 |
| Methionine | 0.17 | 0.06 |
| Phenylalanine | 1.29 | 0.44 |
| Proline | 3.21 | 1.10 |
| Serine | 1.80 | 0.61 |
| Threonine | 1.77 | 0.60 |
| Tryptophan | 0.61 | 0.21 |
| Tyrosine | 1.86 | 0.63 |
| Valine | 1.96 | 0.67 |

The composition of the air-dried solid fraction (using drum drying) is given in Table 6. The fat composition of the crude fat fraction is given in Table 7, wherein the percentages refer to percentages by weight based on the total weight of the crude fat fraction. The amino acid composition of the crude protein is given in Table 8, wherein the percentages refer to percentages by weight based on the total weight of the dried solid fraction. Chitin and chitin-derivatives are comprised in the crude fiber and partly in crude fiber in Table 6.

TABLE 6

| Component | Content (wt. %) |
| --- | --- |
| Moisture (dry matter, 103° C.) | 1.3 |
| Crude protein (Dumas, N × 6.25) | 53.5 |
| Crude fat (after pre-extraction and hydrolysis) | 22.8 |
| Crude ashes (550° C.) | 12.2 |
| Crude fiber (long method) | 13.6 |
| FFA (calculated as oleic acid 282 g/mol) | 0.9 |
| Peroxide value | 2.3 meq/kg fat |

TABLE 6-continued

| Component | Content (wt. %) |
| --- | --- |
| Energy value, kJ/100 g | 1762 |
| Phosphorus, mg/kg (ICP-OES) | 12300 |
| Calcium, mg/kg (ICP-OES) | 38000 |

TABLE 7

| Fatty acid | Content (wt. %) |
| --- | --- |
| C8:0 | <0.1 |
| C10:0 | 1.0 |
| C12:0 | 36.4 |
| C14:0 | 6.4 |
| C14:1 | 0.2 |
| C15:0 | 0.2 |
| C16:0 | 16.9 |
| C16:1 | 2.9 |
| C17:0 | 0.1 |
| C18:0 | 3.0 |
| C18:1 | 19.4 |
| C18:1 cis | 0.4 |
| C18:2 | 9.0 |
| C18:3n3 | 1.0 |
| C20:0 | 0.2 |
| C20:1 | <0.1 |
| C20:3n3 | 0.2 |
| C20:5 | 0.3 |
| C22:0 | 0.2 |
| trans fatty acids | <0.1 |
| saturated fatty acids | 64.4 |
| mono unsaturated fatty acids | 23.1 |
| poly unsaturated fatty acids | 10.5 |
| unsaturated fatty acids | 33.6 |
| omega-3 fatty acids | 1.5 |
| omega-6 fatty acids | 9.0 |
| omega-9 fatty acids | 19.5 |
| omega-3/omega-6 | 0.2 |

TABLE 8

| Amino acid | Content (wt. %) | Content relative to lysine (wt/wt) |
| --- | --- | --- |
| Alanine | 3.53 | 1.12 |
| Asparagine | 2.50 | 0.80 |
| Aspartic acid | 4.74 | 1.51 |
| Cysteine | 0.42 | 0.13 |
| Glutamic acid | 4.99 | 1.59 |
| Glycine | 3.19 | 1.02 |
| Histidine | 1.44 | 0.46 |
| Isoleucine | 2.05 | 0.65 |
| Leucine | 3.58 | 1.14 |
| Lysine | 3.14 | 1.00 |
| Methionine | 0.99 | 0.32 |
| Phenylalanine | 1.99 | 0.63 |
| Proline | 3.22 | 1.03 |
| Serine | 2.31 | 0.74 |
| Threonine | 2.09 | 0.67 |
| Tryptophan | 0.76 | 0.24 |
| Tyrosine | 3.21 | 1.02 |
| Valine | 3.21 | 1.02 |

Example 2

Example 1 was repeated except that the larvae water and solid containing fraction were combined, further reduced in size and then spray-dried to obtain a combined protein meal with the composition as shown in Table 9.

The fat composition of the crude fat fraction of the protein material is given in Table 10, wherein the percentages refer to percentages by weight based on the total weight of the crude fat fraction. The amino acid composition of the crude protein is given in Table 11, wherein the percentages refer to percentages by weight based on the total weight of the dried protein material. The amino acid profile is determined according to the method NEN-EN-ISO 13903.

TABLE 9

| Component | Content (wt. %) |
| --- | --- |
| Moisture (dry matter, 103° C.) | 4.0 |
| Crude protein (Dumas, N × 6.25) | 54.7 |
| Crude fat (after pre-extraction and hydrolysis) | 10.2 |
| Crude ashes (550° C.) | 12.9 |
| Crude fiber (long method) | 10.9 |
| FFA (calculated as oleic acid 282 g/mol) | 0.1 |
| Peroxide value | 1.5 meq/kg fat |
| Energy value, kJ/100 g | 1350 |

TABLE 10

| Fatty acid | Content (wt. %) |
| --- | --- |
| C10:0 | 1.2 |
| C12:0 | 42.5 |
| C14:0 | 7.5 |
| C14:1 | 0.3 |
| C15:0 | 0.2 |
| C16:0 | 15.6 |
| C16:1 | 2.8 |
| C17:0 | <0.1 |
| C18:0 | 2.3 |
| C18:1 | 17.5 |
| C18:1 cis | 0.2 |
| C18:2 | 7.8 |
| C18:3n3 | 1.0 |
| C20:5 | 0.3 |
| trans fatty acids | <0.1 |
| saturated fatty acids | 69.3 |
| mono unsaturated fatty acids | 20.8 |
| poly unsaturated fatty acids | 9.1 |
| unsaturated fatty acids | 29.9 |
| omega-3 fatty acids | 1.3 |
| omega-6 fatty acids | 7.8 |
| omega-9 fatty acids | 17.5 |
| omega-3/omega-6 | 0.2 |

TABLE 11

| Amino acid | Content (wt. %) | Content relative to lysine (wt/wt) |
| --- | --- | --- |
| Alanine | 3.40 | 1.10 |
| Asparagine | 2.72 | 0.88 |
| Aspartic acid | 5.02 | 1.62 |
| Cysteine | 0.42 | 0.12 |
| Glutamic acid | 6.39 | 2.07 |
| Glycine | 2.94 | 0.95 |
| Histidine | 1.65 | 0.53 |
| Isoleucine | 2.42 | 0.78 |
| Leucine | 3.84 | 1.24 |
| Lysine | 3.09 | 1.00 |
| Methionine | 0.94 | 0.30 |
| Phenylalanine | 4.55 | 1.47 |
| Proline | 3.36 | 1.09 |
| Serine | 2.26 | 0.73 |

TABLE 11-continued

| Amino acid | Content (wt. %) | Content relative to lysine (wt/wt) |
| --- | --- | --- |
| Threonine | 2.20 | 0.71 |
| Tryptophan | 0.78 | 0.25 |
| Tyrosine | 3.52 | 1.14 |
| Valine | 3.40 | 1.10 |

The invention claimed is:

1. A dried protein composition comprising:
at least 50 wt. % of a protein; and
at most 25 wt. % of a fat based on dry total weight of the composition, which is mixed with the protein,
wherein the fat comprises at least 40 wt. % saturated fat based on a total weight of the fat in the composition,
wherein the fat contains at least 7 wt. % lauric acid C12:0 based on a total weight of the fat in the composition,
wherein the protein and the fat are derived from insects or worms and the protein has a pepsin digestibility of at least 50%, as measured by a pepsin-HCl method, and
wherein the composition has a moisture content of less than 8%.

2. The composition according to claim 1, comprising at most 10 wt. % fat based on dry weight.

3. The composition according to claim 1, wherein the protein has a pepsin digestibility of at least 70%, as measured by the pepsin-HCl method.

4. The composition according to claim 1, further comprising at least 4,500 mg/kg Ca based on dry weight.

5. The composition according to claim 1, wherein the composition comprises 2-7 wt. % lysine.

6. The composition according to claim 5, wherein the composition comprises further isoleucine 0.4-0.8, threonine 0.5-0.8, tryptophan 0.1-0.3, and valine 0.5-1.2, as a weight ratio relative to the lysine content.

7. The composition of claim 1, further comprising 2-50 wt. % chitin, based on dry weight.

8. The composition of claim 1, wherein the dried protein composition is derived from an aqueous protein fraction derived from pulp of the insects or worms, wherein insect or worm remains in the pulp have a particle size of less than 0.5 mm.

9. The composition of claim 1, wherein the fat comprises 50 wt. % to 80 wt. % saturated fat based on a total weight of the fat in the composition.

10. The composition of claim 1, wherein the fat comprises 60 wt. % or less unsaturated fat based on a total weight of the fat in the composition.

11. The composition of claim 1, wherein the fat comprises 10 wt. % to 45 wt. % mono unsaturated fatty acids based on a total weight of the fat in the composition.

12. The composition of claim 1, wherein the fat comprises 1 wt. % to 20 wt. % poly unsaturated fatty acids based on a total weight of the fat in the composition.

13. The composition of claim 1, wherein the fat contains 8 wt. % to 60 wt. % lauric acid C12:0 based on a total weight of the fat in the composition.

* * * * *

UNITED STATES PATENT AND TRADEMARK OFFICE
CERTIFICATE OF CORRECTION

PATENT NO. : 11,968,995 B2  
APPLICATION NO. : 16/655956  
DATED : April 30, 2024  
INVENTOR(S) : Tarique Arsiwalla et al.

Page 1 of 1

It is certified that error appears in the above-identified patent and that said Letters Patent is hereby corrected as shown below:

On the Title Page

Column 1, Item (71) Applicant, Lines 1-2, delete "Bühler Insect Technology Solutions AG," and insert -- Bühler AG, --

Signed and Sealed this
Sixteenth Day of July, 2024

Katherine Kelly Vidal
*Director of the United States Patent and Trademark Office*